(12) United States Patent
Schmucker et al.

(10) Patent No.: US 8,925,812 B2
(45) Date of Patent: Jan. 6, 2015

(54) MEDICAL DEVICE TRACKING SYSTEM AND APPARATUS

(71) Applicants: Carol A Schmucker, Traverse City, MI (US); Fred P Schoville, Brighton, MI (US)

(72) Inventors: Carol A Schmucker, Traverse City, MI (US); Fred P Schoville, Brighton, MI (US)

( * ) Notice: Subject to any disclaimer, the term of this patent is extended or adjusted under 35 U.S.C. 154(b) by 0 days.

(21) Appl. No.: 13/834,370

(22) Filed: Mar. 15, 2013

(65) Prior Publication Data

US 2014/0263633 A1 Sep. 18, 2014

(51) Int. Cl.
*G06F 19/00* (2011.01)
*G06Q 30/00* (2012.01)
*G06Q 90/00* (2006.01)
*G06Q 10/08* (2012.01)

(52) U.S. Cl.
CPC .................................. *G06Q 10/0875* (2013.01)
USPC ............................ 235/385; 235/375; 235/487

(58) Field of Classification Search
CPC ....... G06K 19/07; G06K 5/00; G06Q 10/087; G06Q 30/00; G06Q 90/00; G06F 19/00; G06F 17/00; A61M 16/183; A61B 19/44; A61B 5/0031; A61B 5/055; A61B 19/00
USPC .................................. 235/385, 380, 487, 375
See application file for complete search history.

(56) References Cited

U.S. PATENT DOCUMENTS

| | | | |
|---|---|---|---|
| 2009/0037244 A1* | 2/2009 | Pemberton | 705/8 |
| 2009/0277959 A1* | 11/2009 | Grimard | 235/380 |
| 2009/0317002 A1* | 12/2009 | Dein | 382/224 |

* cited by examiner

*Primary Examiner* — Edwyn Labaze
(74) *Attorney, Agent, or Firm* — Mitchell Law PLLC; Matthew W. Mitchell

(57) ABSTRACT

A method for tracking medical devices and tools in a medical environment is disclosed. The method includes registering a plurality of radio frequency identification (RFID) tags with a plurality of medical tools, generating an item list comprising a set of medical tools, wirelessly sensing the RFID tags associated with an assembled set of medical tools, assembled in preparation of a medical procedure based upon the generated item list, deciding, if the RFID tags associated with the assembled medical tools is sensed, that the medical device or tool is present in the assembled set of the medical tools, generating a checked-in list of medical tools based upon the deciding, accounting medical tools assembled for check-out by wirelessly sensing the RFID tags associated with the medical tools assembled for check-out, and displaying a list of medical tools associated with the checked-in list and not included in the accounting.

18 Claims, 14 Drawing Sheets

FIG. 11

MEDICAL DEVICE TRACKING SYSTEM AND APPARATUS

TECHNICAL FIELD

This disclosure relates to medical devices, and more particularly to tracking medical devices, tools, and supplies in a medical environment.

BACKGROUND

The statements in this section merely provide background information related to the present disclosure and may not constitute prior art.

In a medical environment, technicians and medical personnel must prepare surgical instruments and various medical devices in anticipation of a medical procedure. In many hospitals and other medical environments, an inventory list of necessary equipment is generated from which a set of medical devices including surgical tools is assembled. Technicians typically must match the medical devices instruments against the written list when assembling instrument sets for sterilization after they are received from the washers. The process can be time-consuming and is prone to human error. In some cases, identifying marks and other identifying indicia can be difficult to discern.

In an operating room environment, prior to the start of the surgery, a circulating nurse and a surgical technologist must verify the correctness of the total number and accuracy of the instruments present by the nurse. A written list is used containing instruments that are entered into the instrument set. Comparison and verification is made by: a reading by the nurse to the technologist and verification with the technologist at the actual instrument. This process, especially when multiple sets and specialty instruments are necessary, can be particularly inefficient and susceptible to human-error. When additional instrumentation is required during the surgery, the circulating nurse must add these instruments to the written count.

Therefore, a need exists for a medical device tracking system and apparatus to track medical devices such as surgical tools and supplies in a medical environment such as an operating room.

SUMMARY

A method and system for tracking medical devices, tools, and supplies in a medical environment is disclosed. The method includes registering a plurality of radio frequency identification (RFID) tags with a plurality of medical tools, generating an item list comprising a set of medical tools, wirelessly sensing the RFID tags associated with an assembled set of medical tools, assembled in preparation of a medical procedure based upon the generated item list, deciding, if the RFID tags associated with the assembled medical tools is sensed, that the medical device or tool is present in the assembled set of the medical tools, generating a checked-in list of medical tools based upon the deciding, accounting medical tools assembled for check-out by wirelessly sensing the RFID tags associated with the medical tools assembled for check-out, and displaying a list of medical tools associated with the checked-in list and not included in the accounting.

In a medical environment such as a hospital, the system for tracking medical devices and tools may be utilized to ensure that requested sets of medical tools are assembled and prepared for use in a medical procedure. The system enables hospital personnel to verify completeness of the assembly prior to the medical procedure or sterilization. In one such exemplary environment, a mobile device is utilized to scan in RFID tags associated with a plurality of medical tools. The mobile device scans in the RFID tag information, the system then determines that the medical tools have been assembled completely according to a requested item list. The medical tools may then be transported to an operating room. There, the medical tools may be scanned a second time, generating a checked-in list. During the medical procedure various tools may be added or subtracted to the checked-in list according to needs of the medical personnel. Before completing a medical procedure it is sometime necessary to account for all of the medical tools utilized in a procedure. For example, before closing a surgical wound the checked-in medical tools are preferentially accounted. A mobile device taught herein quickly accounts for the medical tools and may be utilized to identify any "missing" tools.

This summary is provided merely to introduce certain concepts and not to identify key or essential features of the claimed subject matter.

BRIEF DESCRIPTION OF THE DRAWINGS

One or more embodiments will now be described, by way of example, with reference to the accompanying drawings, in which:

FIG. 9-13 show various user interfaces, in accordance with the present disclosure.

DETAILED DESCRIPTION

Figure 1:
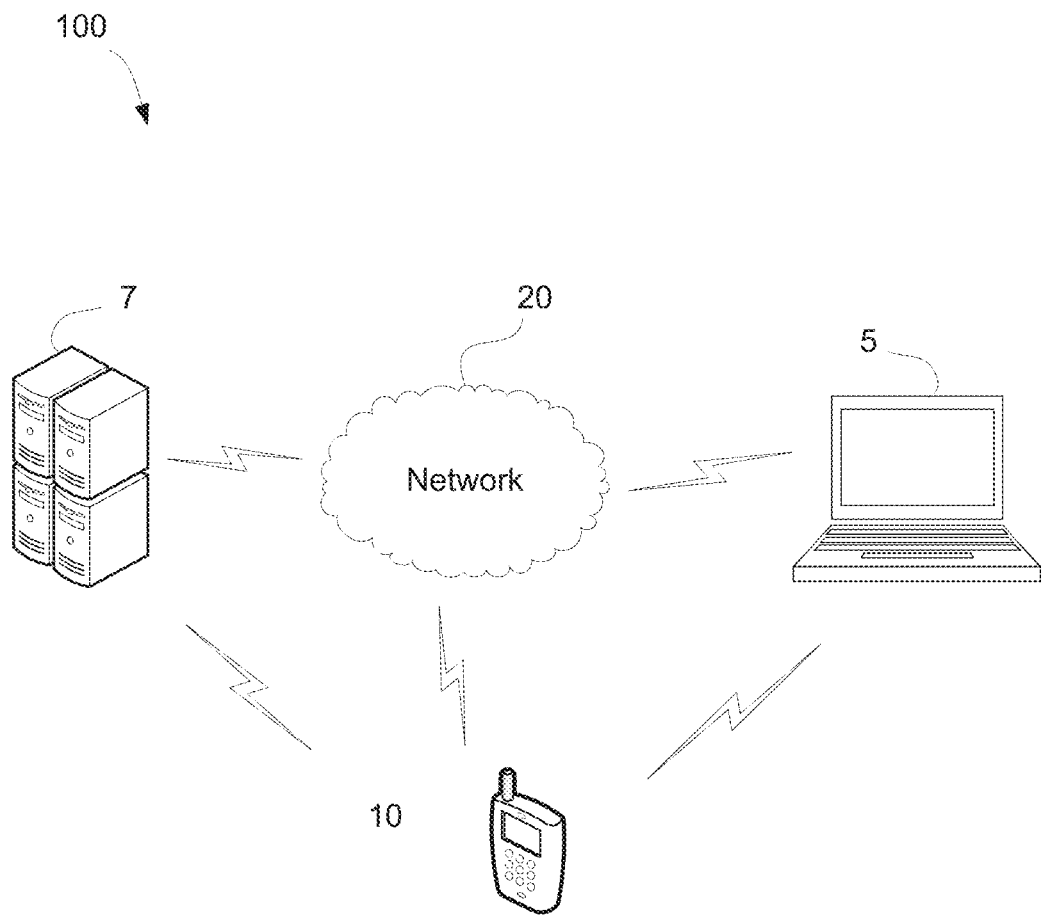
FIG. 1 schematically shows an exemplary medical device tracking system, in accordance with the present disclosure.

Various embodiments of the present invention will be described in detail with reference to the drawings, where like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

Referring now to the drawings, wherein the depictions are for the purpose of illustrating certain exemplary embodiments only and not for the purpose of limiting the same, FIG. 1 schematically shows an exemplary medical device tracking system 100 that may help implement the methodologies of the present disclosure. The system 100 includes a computing device 5, a server system 7, a network 20, and a mobile tracking device 10. As shown in FIG. 1, the computing device 5 may be directly communicatively connected to the mobile device 10 via the network 20 and/or directly communicatively connected to the mobile device 10. The server system 7 may be directly communicatively connected to the mobile device 10 and the computing device 5 via the network 20 and/or directly communicatively connected to the mobile device 10. The mobile device 10 may be physically connected to the network 20 or the computing device 5 during selected periods of operation without departing from the teachings herein. The disclosure herein can be applied with or without use of the network 20 and is therefore not intended to be limited to thereby. Components of the medical device tracking system 100 are shown in FIG. 1 as single elements. Such illustration is for ease of description and it should be recognized that the system 100 may include multiple additional implementations of the components, e.g., the mobile device 10 and the computing device 5 may be a single device.

The network 20 may be any suitable series of points or nodes interconnected by communication paths. The network 20 may be interconnected with other networks and contain sub networks network such as, for example, a publicly accessible distributed network like the Internet or other telecommunications networks (e.g., intranets, virtual nets, overlay networks and the like). The network 20 may facilitates the exchange of data between and among the mobile device 10, the computing device 5, and the server system 7 although in various embodiments the mobile device 10 may be directly connected to the computing device 5.

The server system 7 may be one or more of various embodiments of a computer including high-speed microcomputers, minicomputers, mainframes, and/or data storage devices. The server system 7 preferably executes database functions including storing and maintaining a database and processes requests from the mobile device 10 and the computing device 5 to extract data from, or update, a database as described herein below. The server 7 may additionally provide processing functions for the mobile device 10 and the computing device 5 as will become apparent to those skilled in the art upon a careful reading of the teachings herein.

In addition, the mobile device 10 may include one or more applications that the user may operate. Operation may include downloading, installing, turning on, unlocking, activating, or otherwise using the application. The application may comprise at least one of an algorithm, software, computer code, and/or the like, for example, mobile application software. In the alternative, the application may be a website accessible through the world wide web.

Figure 2:
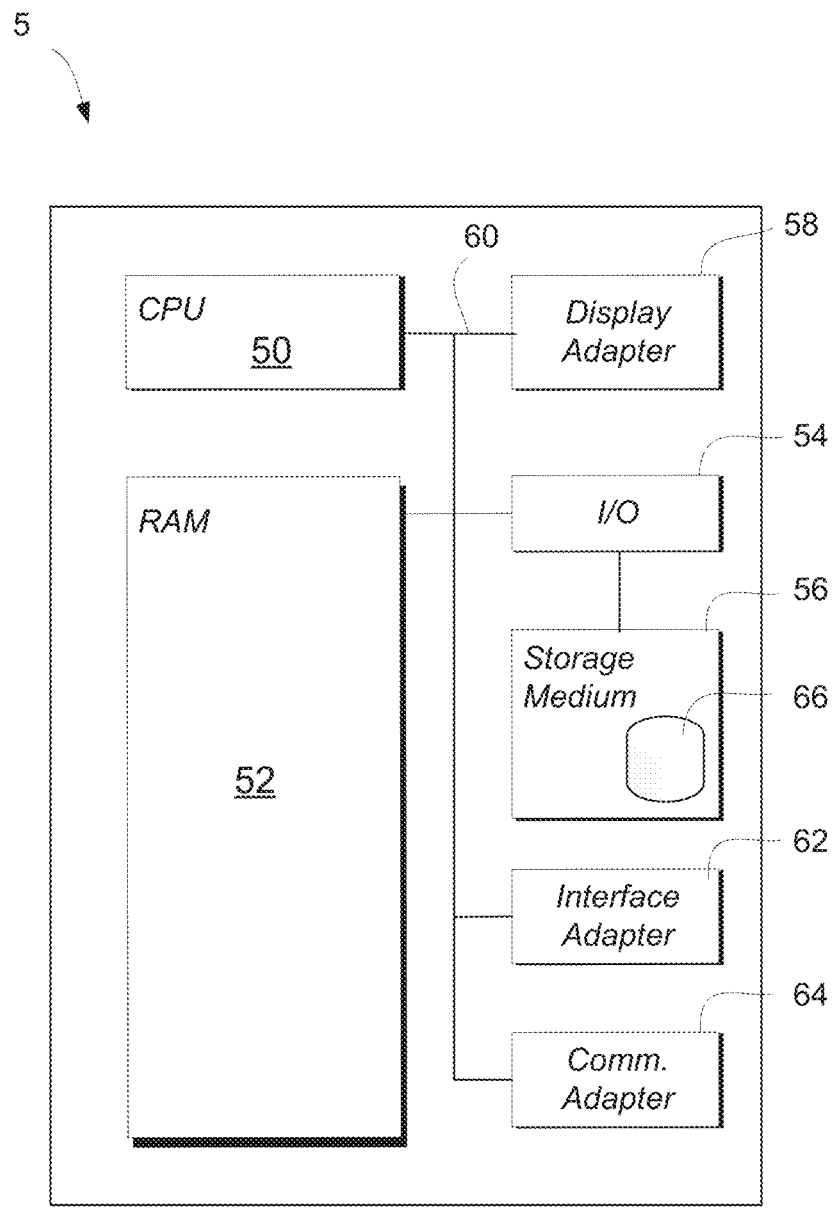
FIG. 2 schematically shows an exemplary computing device, in accordance with the present disclosure.

FIG. 2 shows the exemplary computing device 5. The computing device 5 includes a central processing unit (CPU) 50, random access memory (RAM) 52, input/output circuitry 54 for connecting peripheral devices such as a storage medium 56 to a system bus 60, a display adapter 58 for connecting the system bus 60 to a display device, a user interface adapter 62 for connecting user input devices such as a keyboard, a mouse, and/or a microphone, to the system bus 60, and a communication adapter 64 for connecting the computing device 5 to the network 20. In one embodiment, the communication adapter 64 is a wireless adapter configured for extraterrestrial communication such as in a communications satellite. The storage medium 56 is configured to store, access, and modify a database 66, and is preferably configured to store, access, and modify structured or unstructured databases for data including, for example, relational data, tabular data, audio/video data, and graphical data.

The central processing unit 50 is preferably one or more general-purpose microprocessor or central processing unit(s) and has a set of control algorithms, comprising resident program instructions and calibrations stored in the memory 52 and executed to provide the desired functions including parallel processing functions. As one skilled in the art will recognize, the central processing unit 50 may have any number of processing "cores" or electronic architecture configured to execute processes in parallel. In one embodiment, an application program interface (API) is preferably executed by the operating system for computer applications to make requests of the operating system or other computer applications. The description of the central processing unit 50 is meant to be illustrative, and not restrictive to the disclosure, and those skilled in the art will appreciate that the disclosure may also be implemented on platforms and operating systems other than those mentioned.

Figure 3:
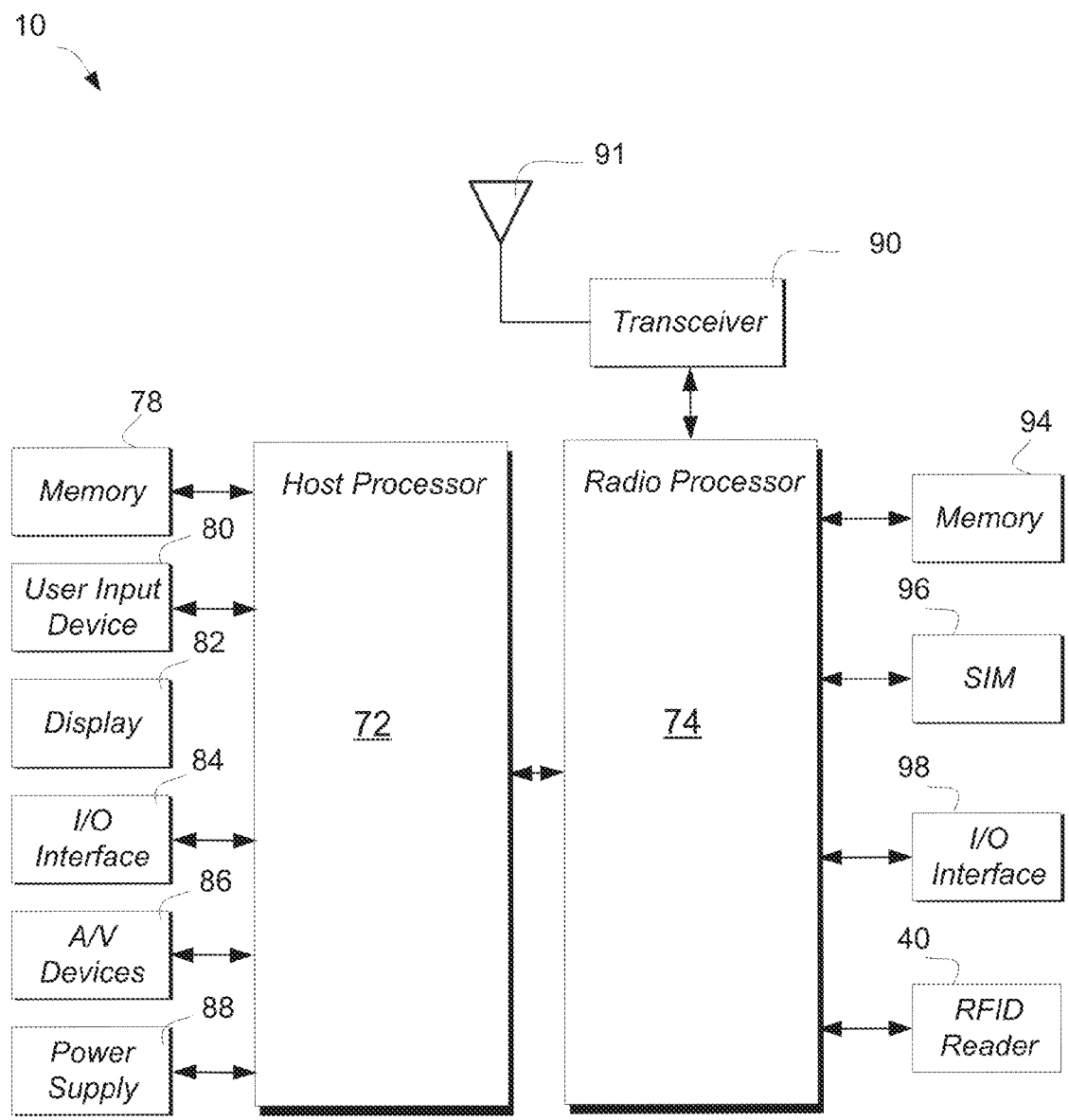
FIG. 3 schematically shows an exemplary mobile device, in accordance with the present disclosure.

FIG. 3 schematically shows an exemplary embodiment of the device 10 configured to operate in a mobile environment. As shown in FIG. 3, the device 10 may include a dual processor architecture, including a host processor module 72 and a radio processor 74 (e.g., a base band processor or modem). The host processor module 72 and the radio processor 74 may be configured to communicate with each other using an interface 76. The device 10 may additionally include any digital and/or analog circuit elements, comprising discrete and/or solid state components, suitable for use with the embodiments disclosed herein. One skilled in the art will recognize upon a careful reading of the teachings herein that the radio processor may be omitted in a wired embodiment of the device 10.

The host processor module 72 may be configured to execute various computer programs (e.g., software, firmware, or other code) such as application programs and system programs to provide computing and processing operations for the device 10. The radio processor 74 may be responsible for performing data communications operations for device 10 such as transmitting and receiving data information over one or more wireless communications channels. Although the host processor module 72 and the radio processor 74 are shown and described as separate processors, such an illustration is for ease of description and it should be recognized that the functions performed by the host processor module 72 and the radio processor 74 may be combined on a single chip.

In various embodiments, host processor module 72 may be implemented as a host central processing unit ("CPU") using any suitable processor or logic device, such as a general purpose processor, or other processing device in alternative embodiments configured to provide processing or computing resources to device 10. For example, host processor module 72 may be responsible for executing various computer programs such as application programs and system programs to provide computing and processing operations for device 10. The application software may provide a graphical user interface ("GUI") to communicate information between device 10 and a user. The computer programs may be stored as firmware on a memory associated with processor 72, may be loaded by a manufacturer during a process of manufacturing device 10, and may be updated from time to time with new versions or software updates via wired or wireless communication.

System programs assist in the running of a computer system. System programs may be directly responsible for controlling, integrating, and managing the individual hardware components of the computer system. Examples of system programs may include, for example, an operating system, a kernel, device drivers, programming tools, utility programs, software libraries, an application programming interface ("API"), a GUI, and so forth.

The memory module 78 is preferably coupled to the host processor module 72. In various embodiments, the memory module 78 may be configured to store one or more computer programs to be executed by the host processor module 72. The memory module 78 may be implemented using any machine-readable or computer-readable media capable of storing data such as volatile memory or non-volatile memory, removable or non-removable memory, erasable or non-erasable memory, writeable or re-writeable memory, and so forth. Although the memory module 78 is shown as being separate from the host processor module 72 for purposes of illustration, in various embodiments some portion or the entire memory module 78 may be included on the same integrated circuit as the host processor module 72. Alternatively, some portion or the entire memory module 78 may be disposed on an integrated circuit or other medium (e.g., solid state drive) external to the integrated circuit of the host processor module 72.

A user input device 80 may be coupled to the host processor module 72. The user input device 80 may include, for example, an alphanumeric, numeric key layout and an integrated number dial pad. The device 10 also may include various keys, buttons, and switches such as, for example, input keys, preset and programmable hot keys, left and right action buttons, a navigation button such as a multidirectional navigation button, power/end buttons, preset and programmable shortcut buttons, a volume rocker switch, a ringer on/off switch having a vibrate mode, a keypad and so forth.

The host processor module 72 may be coupled to a display device 82. The display device 82 may include any suitable visual interface for displaying content to a user of the device 10, such as a liquid crystal display ("LCD") such as a touch-sensitive color (e.g., 16-bit color) thin-film transistor ("TFT") LCD screen. In some embodiments, the touch-sensitive LCD may be used with a stylus and/or a handwriting recognizer program.

An I/O interface 84 is preferably coupled to the host processor module 72. The I/O interface 84 may include one or more I/O devices such as a serial connection port, an infrared port, wireless capability, and/or integrated 802.11x (WiFi) wireless capability, to enable wired (e.g., USB cable) and/or wireless connection to a local or networked computer system, such as a workstation client, and/or the server 5.

In one embodiment, the device 10 includes an audio/video ("A/V") module 86 coupled to the host processor module 72 for communicatively connecting and communicating therebetween to various audio/video devices. The A/V module 86 may be configured to support A/V capability of the device 10 including components such as, a microphone, one or more speakers, an audio port to connect an audio headset, an audio coder/decoder (codec), an audio player, a video codec, a video player, and so forth. The A/V input module 86 may include an imaging module configured to capture digital images. The imagining module may include an optical sensor, e.g., a charged coupled device (CCD) or a complementary metal-oxide semiconductor (CMOS) optical sensor to facilitate camera functions, such as recording photographs and video clips. The image frames may be processed by the memory 78 or displayed on the display 82.

A power supply 88 configured to supply and manage power to components of device 10 is preferably coupled to the host processor module 72. In various exemplary embodiments, the power supply 88 may be implemented by a rechargeable battery, such as a removable and rechargeable lithium ion battery to provide direct current ("DC") power, and/or an alternating current ("AC") adapter to draw power from a standard AC main power supply.

As described herein above, the radio processor 74 may perform voice and/or data communication operations for the device 10. For example, the radio processor 74 may be configured to communicate voice information and/or data information over one or more assigned frequency bands of a wireless communication channel. The radio processor 74 may be implemented as a communications processor using any suitable processor or logic device, such as a modem processor or baseband processor. The radio processor 74 may include, or be implemented as, a digital signal processor ("DSP"), a media access control ("MAC") processor, or any other type of communications processor in accordance with the described embodiments. Memory 94 may be coupled to the radio processor 74. Although memory 94 is shown as being separate from and external to the radio processor 74 for purposes of illustration, in various embodiments some portion may be included on the same integrated circuit as the radio processor 74. Further, the host processor module 72 and the radio processor 74 may share a single memory.

The device 10 may include one or more transceivers 90 coupled to the radio processor 74, each transceiver 90 may be configured to communicate using a different types of protocol, communication ranges, operating power requirements, RF sub-bands, information types (e.g., voice or data), use scenarios, applications, and so forth. For example, the transceiver 90 may include a Wi-Fi transceiver and a cellular or WAN transceiver configured to operate simultaneously. The transceiver 90 may be implemented using one or more chips as desired for a given implementation. Although transceiver 90 is shown as being separate from and external to the radio processor 74 for purposes of illustration, in various embodiments some portion may be included on the same integrated circuit as the radio processor 74. The transceiver is preferably connected to an antenna 91 for transmitting and/or receiving electrical signals. As shown in FIG. 3, the antenna 91 may be coupled to the radio processor 74 through transceiver 90.

A SIM device 96 may be coupled to radio processor 74. The SIM device 96 may be implemented as a removable or non-removable smart card configured to encrypt voice and data transmissions and to store user-specific data for allowing a voice or data communications network to identify and authenticate the user. The SIM device 96 also may store data such as personal settings specific to the user.

An I/O interface 98 may be coupled to the radio processor 74. The I/O interface 98 may include one or more I/O devices to enable wired (e.g., serial, cable, etc.) and/or wireless (e.g., WiFi, short range, etc.) communication between the device 10 and one or more external computer systems.

A radio-frequency identification (RFID) reader 40 may be coupled to the radio processor 74 or the host processor 72. In one embodiment, functions of the RFID reader 40 are incorporated into the radio processor 72 enabling the mobile device 10 to utilizes the transceiver 90 and antenna 91 to carry out functions of the RFID reader 40. The RFID reader 40 is configured to read identification information stored on an RFID tag by use of radio waves. In one embodiment, an RFID tag is formed of a microchip that is attached to an antenna and upon which is stored a unique digital identification number.

Figure 4:
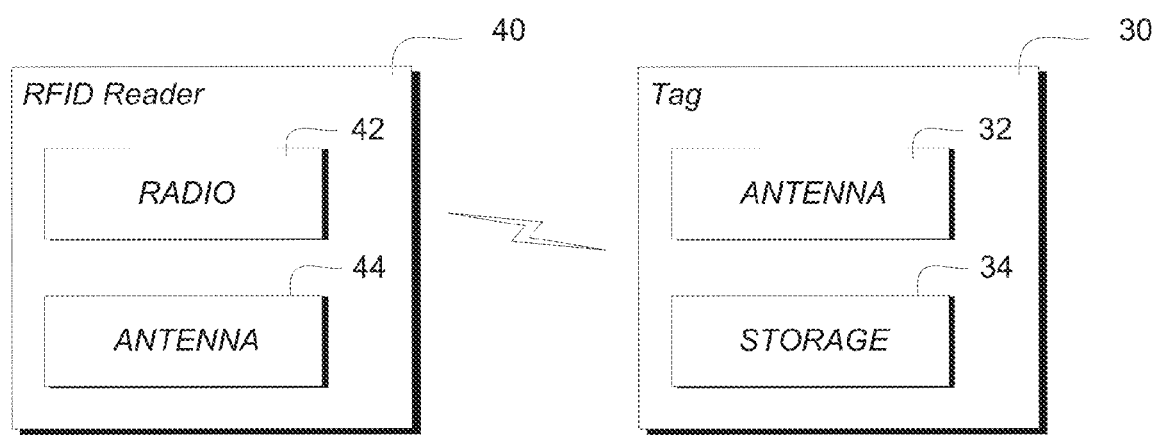
FIG. 4 schematically shows an exemplary RFID reader of the mobile device communicating with an exemplary RFID tag, in accordance with the present disclosure.
Figure 5A:
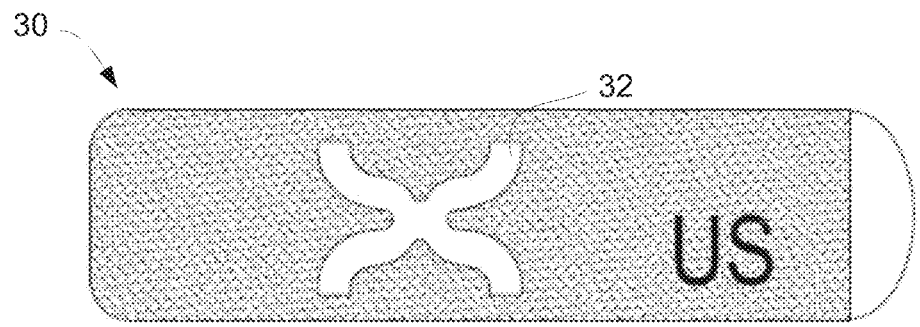
FIGS. 5A and 5B and FIGS. 6A and 6B show various embodiments of an RFID tag, in accordance with the present disclosure.
Figure 5B:
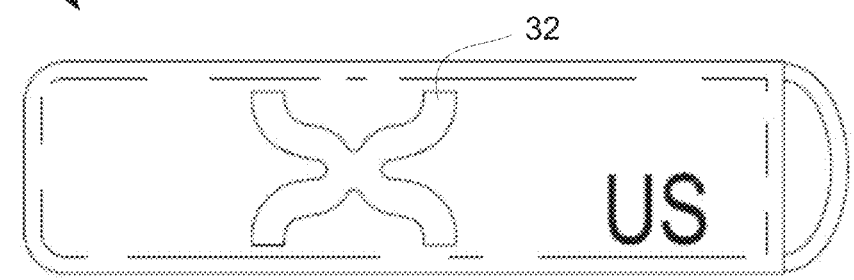
Figure 6A:
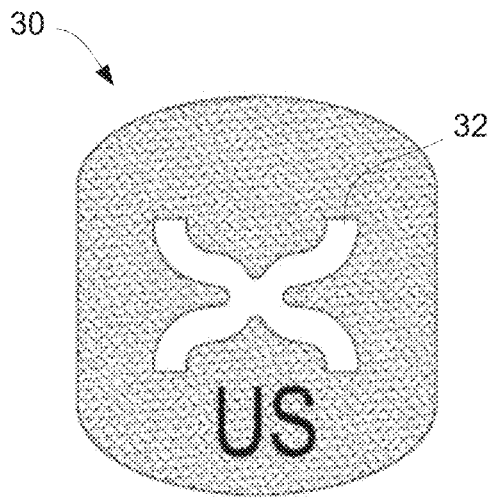
Figure 6B:
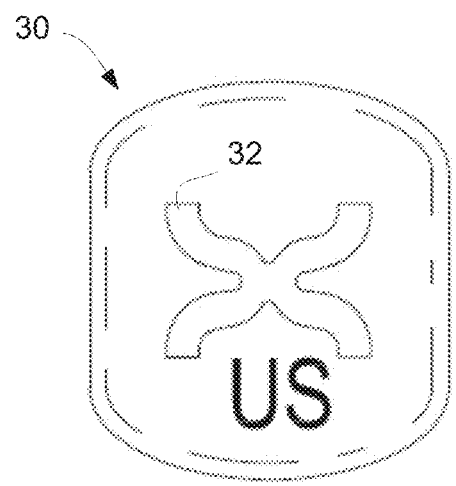

FIG. 4 schematically shows an exemplary RFID reader 40 communicating with an exemplary RFID tag 30. As FIG. 4 shows, the RFID reader 40 may include a radio 42 for transmitting radio carrier signals and an antenna 44 for receiving radio signals from an RFID tag 30. Components of the RFID reader 40 and the RFID tag 30 are shown in FIG. 4 as single elements. Such illustration is for ease of description and it should be recognized that the components may be combined in one or more devices and/or integrated chips. As used herein, the RFID tag 30 may be of one of a well-known RFID tag type such as a magnetically coupled RFID tag, an electrically coupled RFID tag or a multiple frequency RFID tag. Correspondingly, an antenna array used to sense RFID tags may be comprise antenna elements for sensing using magnetic or electrical or multiple frequency coupling with RFID tags. The electrical field generated by the antenna 44 may be constant or activated by actuation means, such as a sensor or a trigger. The radio 42 may be configured to utilize the antenna 44 to emit the radio carrier signals. In one embodiment, a decoder may be utilized by the RFID reader 40 for decoding data received by the RFID tag 30.

The RFID reader 40 is a transmitter/receiver that reads the contents of RFID tags such as exemplary RFID tag 30 that are in the vicinity of the reader 40. For example, RFID reader 40 reads the contents of the RFID tag 30 that is in the vicinity of RFID reader 40. RFID reader 40 converts the radio waves reflected back from RFID tag 30 via an antenna 32 into digital data that may then be conveyed to the computing device 5, which may utilize the information. The RFID reader 40 and the RFID tag 30 may be configured to operate using inductive coupling, electrostatic coupling, or electromagnetic coupling, in which induction of a current in a coil, induction of a voltage on a plate, or a magnetic field, respectively, may be used as a means for transferring data and/or power. The operational distance between the RFID reader 40 and the RFID tag 30 depends on the particular hardware configurations, as well as the frequency and power of the transmitted signals.

Each RFID tag 30 may be programmed with unique information, such as encoded data that includes an identifying code corresponding to store information. For example, a 64 to 256 bit code, may contain the following data: company identification number, product number, and unique serial number. In one embodiment of the RFID tag, information may be stored in a storage module 34. The storage 34 may comprise any suitable type of storage medium such as random access memory (RAM), flash memory, electrically erasable read-only memory (EEPROM), etc., and/or combinations thereof.

FIGS. 5A and 5B and FIGS. 6A and 6B show various embodiments of an RFID tag 30. In certain configurations, the RFID tag 30 is a planar label configured for adhesion on a medical tool or device. The RFID tags 30 may, for example, be adhered to printed, flexible labels that may be pasted or adhered onto a surface. As described herein above, the RFID tag 30 includes an antenna 32 used for radio communication with the RFID reader 40. The antenna 32 is, for example, a coil for magnetic field communication and a dipole antenna for electric field communication. The RFID tags 30 do not require line-of-sight and may be embedded within objects or packages. The RFID tags 30 preferably have no internal power supply enabling the tags 30 to be affixed to small medical devices, tools, and supplies. The minute electrical current induced in the antenna 32 by the incoming radio frequency signal provides sufficient power for the integrated circuit in the tag to power up and transmit back (backscatter) a response. In one embodiment, active or semi-passive RFID tags may be utilized consistent with the teachings here, such as in larger medical devices and tools. As used herein, references to "medical tools" "medical devices" or supplies are analogous references and may be used interchangeably when used in context to the items tracked by the system.

Figure 7:
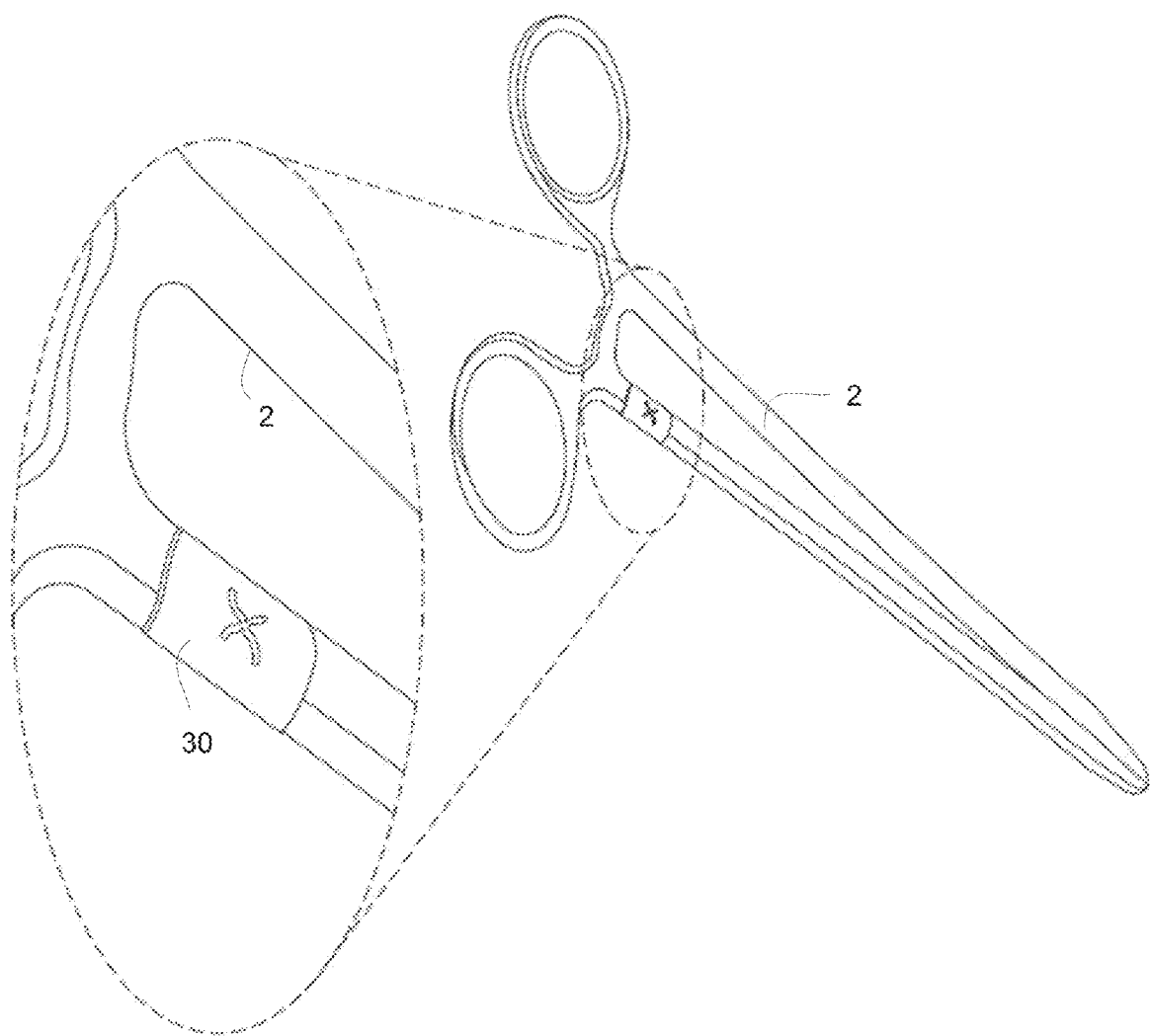
FIG. 7 shows an exemplary medical tool having an adhered RFID tag 30 adhered on a surface thereof, in accordance with the present disclosure.

FIG. 7 shows an exemplary medical tool 2 having an adhered RFID tag 30 adhered on a surface thereof. As FIG. 7 shows, the RFID tag 30 may be sized and adapted for minimal obstruction on the medical tool. The RFIG tag 30 and unique identifier associated therewith may correspond to an information profile stored in a database associated with the tracking system 100. A profile may, for example, include profiled object data. Profiled object data is any data or information about profiled object 110 that may be contained in the profile. For example, the profiled object data may include a name, identification number, serial number, and description of profiled object. However, it should be noted that illustrative embodiments may include any necessary information to identify and describe profiled object within the profiled object data.

Further, the profile may include specific dates and times for when profiled object is to be scanned for an inventory count and the specific location of profiled object within the entity. Furthermore, the profile may include instructions as to how the system 100 is to perform the inventory count of profiled object. For example, a particular profiled object may represent one or more objects, each of which includes an RFID tag, such as the RFID tag 30. Consequently, the profile instructs the system 100 to count each individual profiled object.

Figure 8:
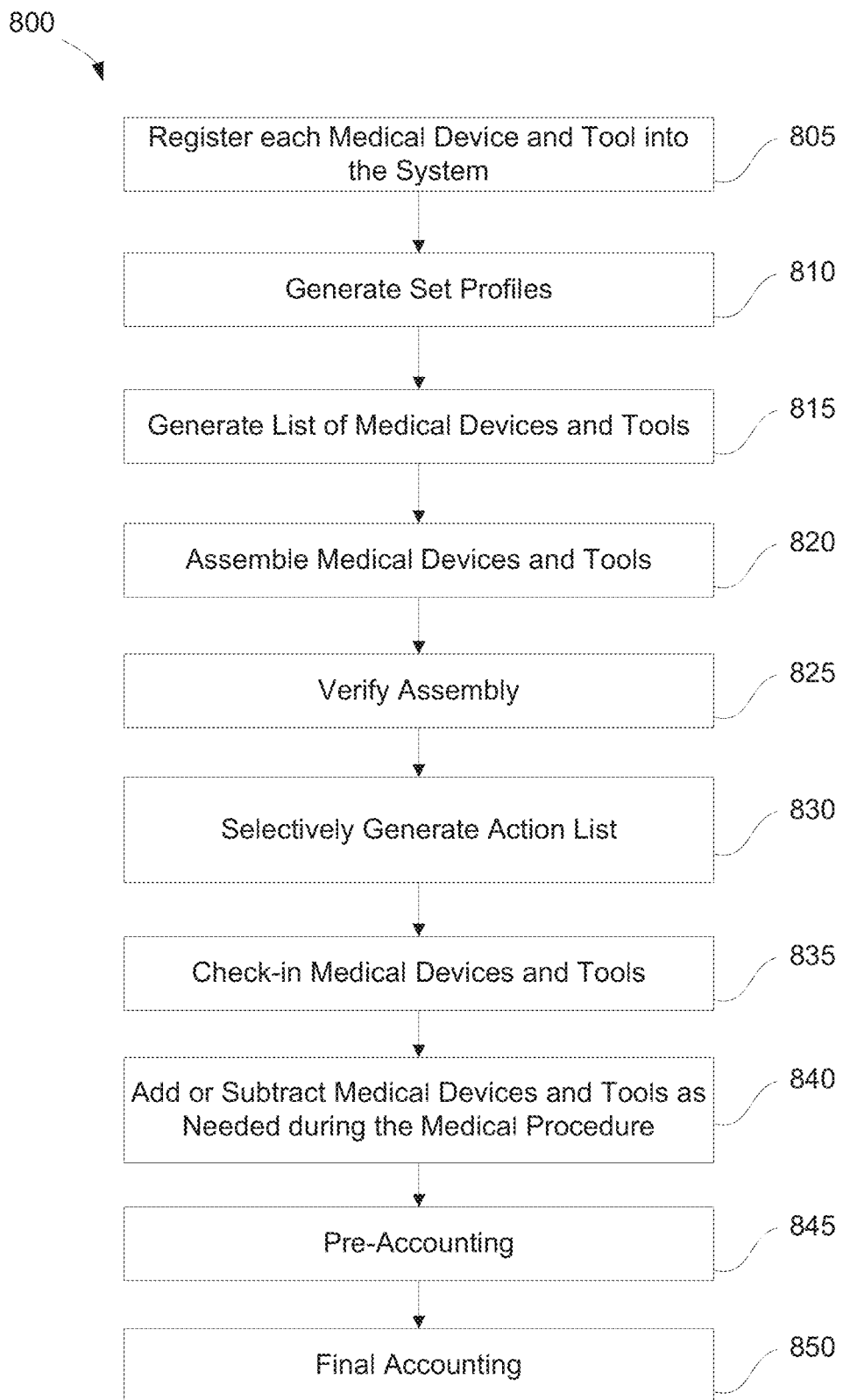
FIG. 8 shows an exemplary control scheme for tracking and managing medical device inventory, in accordance with the present disclosure.

FIG. 8 shows an exemplary control scheme 800 for tracking and managing medical device inventory. Various functions of the control scheme 800 may be executed on the computing device 5 and/or the mobile device 10. Initially, each medical device and tool is registered 805 by assigning a unique identification identifier such as a numeric or alphanumeric identifier. In one embodiment, a user can enter multiple RFID tag identification values in a database in communication with the computing device 5 and associate the multiple RFID tag identification values with a single inventory item. While the disclosure herein is directed at an RFID tags and identification, as consistent with the teachings herein, each medical tool may have additional EEprom memory chips, 2D bar code, 1D bar code, etched dot matrix, magnetic memory tape, and RFID powder for identifying the medical tool. One skilled in the art, upon a careful study of the teachings herein, may apply or incorporate the teachings of the RFID tracking system and RFID tracking system functions to read and identify medical tools having identification means incorporated into EEprom memory chips, 2D bar code, 1D bar code, etched dot matrix, magnetic memory tape, and RFID powder.

After registration, one or more profiles may be generated each having a set of medical devices and tools associated therewith 810. Each profile may correspond to a medical procedure or room in a hospital, for example. In this way, a list of required medical tools may be created or recalled quickly by hospital staff. For example, a heart transplant procedure requires a particular set of medical tools and devices to be available and ready for the surgeons during the procedure. By associating the set of tools with a profile and associating the profile with the operation, the list of tools may be quickly assembled by staff in preparation for the procedure.

In one embodiment, an item list of tools for a procedure may be generated based upon a predetermined profile, a manually entered list, or a list generated previously 815. Tools and medical devices may be readily added or subtracted from a generated list for particular doctor preferences or special requests. Once the item list is generated by the technician or user-operator, the item set is preferably given a unique surgery set ID. The surgery set will be loaded in a database an electronic record will be kept of the surgery set. The record can include a video and instrument number of the set.

Once the item list is generated a technician may assemble and prepare the medical devices and tools on the item list 820. After assembly of the medical devices and tools, or during the assembly, the technician may verify that the correct devices and tools have been acquired 825. Verification is executed using the mobile device 10. The unique RFID tag positioned on each of the medical devices and tools may be read by the mobile device 10 when positioning or "waving" the mobile device 10 over, or in proximity to, the various medical devices and tools. The system makes a decision regarding the presence or absence of an item in the list by checking if any one of the RFID tags associated with the item are sensed by the mobile device 10 as described herein above.

An action list may be generated that displays any potential extra medical devices and tools that were scanned in, but not requested by the list 830. The action list may also display any potential medical devices and tools that were not scanned and therefore remain unassembled or "missing." The mobile device 10 may selectively display the generated list or the action list in response to a request by the user. After each of the requested medical devices and tools have been properly assembly and verified by the mobile device 10, the technician-user may check-in the medical devices and tools 835. In some medical environments, subsequent to assembling the complete item list, the set of medical tools may be physically transferred to medical room such as a surgery suite. There, a circulating nurse or other user-operator may scan the set of medical tools using the mobile device 10 for check-in 835. In one embodiment, a video display of the surgery set will be displayed on a touch screen to accept or reject. On acceptance of the set as correct, an electronic record will be recorded to the unique surgery set ID that the surgery set was accepted in the surgery suite. Any additional items added during surgery will be added to the electronic surgery set as required. This data will be added to a database for recording. As described herein below, the check-in list may be subsequently utilized after performing the medical procedure to compare the checked-in medical devices and tools with a scanned list of checked-out medical devices and tools.

During the medical procedure, additional medical devices and tools may be necessary that were not included in the list or the checked-in list. The new medical devices and tools may be included by scanning the RFID tag and checking-in the new device or tool. Various devices and tools may be required to enter and exit the medical procedure environment, depending on, or consistent with, a medical environment protocol, these devices and tools may be quickly checked-in and out as needed 840.

Subsequent to a medical procedure, or just prior to in the particular case of a surgery and closing a surgical wound, it is necessary to account for each of the medical devices and tools 845. Accounting is accomplished by scanning the medical devices and tool's RFID tags. The scanned tags are accounted and compared with the checked-in list and any additions or subtractions made during the medical procedure. Similar to above, the system makes a decision regarding the presence or absence of an item in the list by checking if any one of the RFID tags associated with the item are sensed by the mobile device 10. In this way, medical devices and tools may be quickly identified as "missing." If the post-medical procedure scan matches the check-in list including any amendments made during the procedure, a circulating nurse or user-operator can accept the scan and indicate all items accounted for. An electronic record can be recorded indicating that the items have been accounted. If the scan does not match the check-in list including any amendments made during the procedure, the missing devices or tools can be display on the video display showing the particular unscanned items. In some medical environments, the circulating nurse will be required to find the missing item and rescan the set. Once the unscanned or "missing" items are found, an electronic record will be recorded that all items have been accounted for.

Additionally, to prevent loss of instrumentation which currently may occur during clean up, the mobile device 10 can be used again prior to physically taking the medical devices and tools from a medical operating environment to a central processing environment 850. In some medical environments, the unique ID for that medical set will be recorded as completed all steps of the process and returned and marked for availability.

Figure 9:
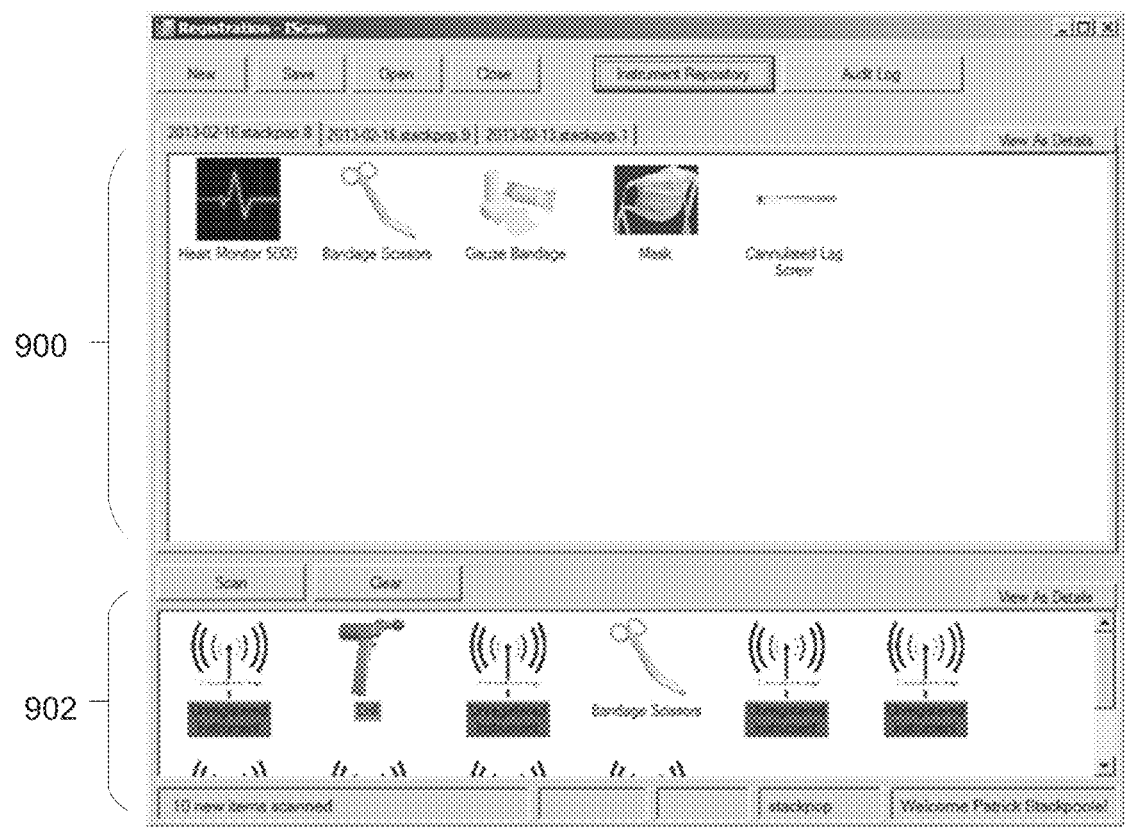

FIG. 9 shows an exemplary user interface for registering each medical device and tool with the system 100. In one embodiment, the user interface is configured to enable a user to register scannable and unscannable instruments and items related to healthcare. The top pane 900 of the exemplary user interface displays items in the currently opened packet while a bottom pane 902 shows the recently scanned items. The bottom scan pane is populated when the Scan button is clicked and RFID-enabled items are within range of the connected scan reader. Items can be drag-dropped from the bottom pane to the top.

Figures 10A, 10B:
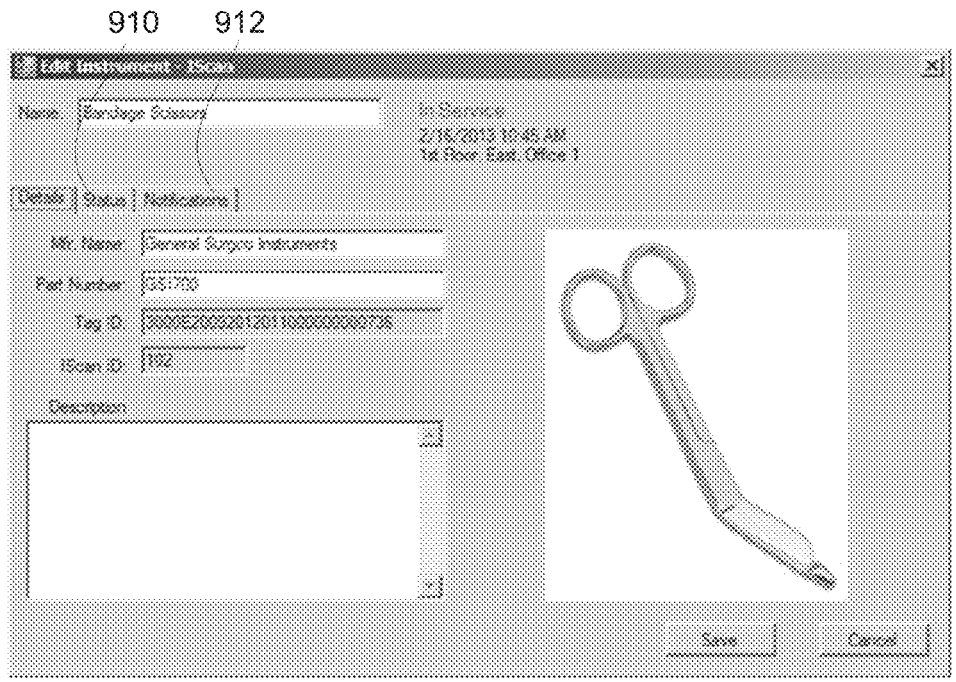
Figure 10C:
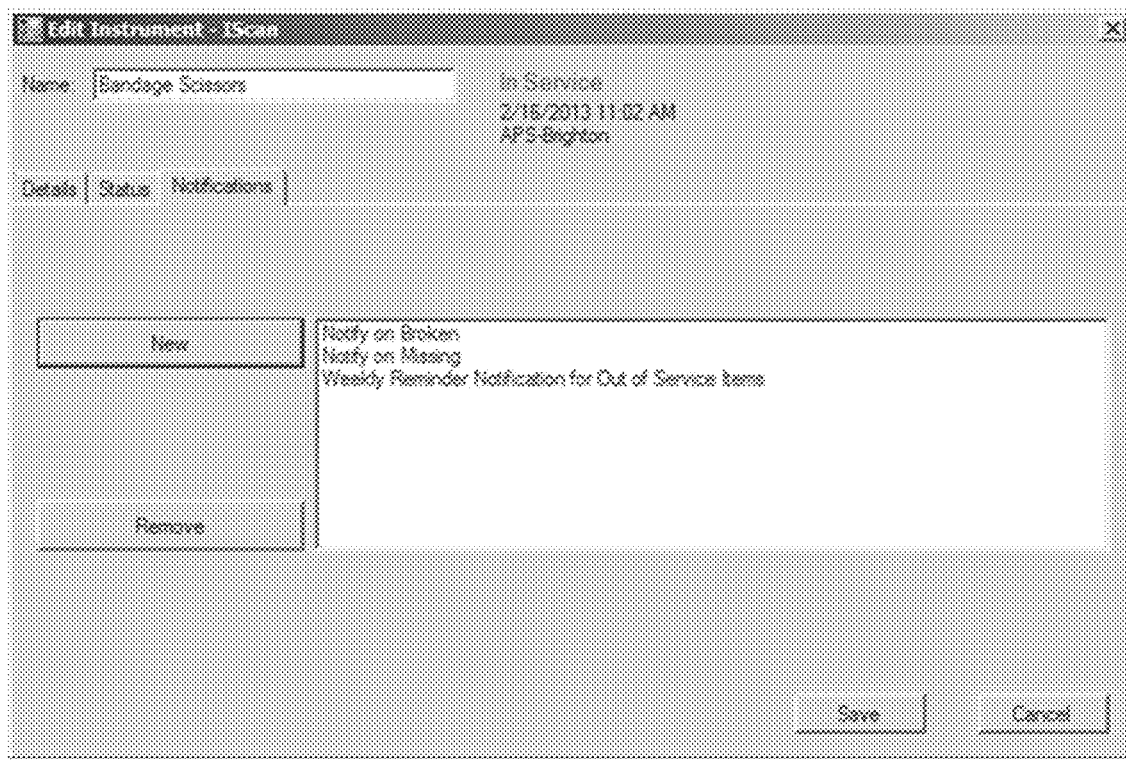

FIGS. 10A-10C show exemplary user interfaces for uploading and editing information associated with a particular instrument. In one embodiment, the user interface of FIG. 10A may be accessed by navigating from an icon shown in another user interface window. Accessing may be made in the usual way, e.g., via mouse input or touch in a touch screen implementation. In one embodiment, a user may input or edit an item name, manufacturer, part number, image, and description. Additional tabs may be included for different functionality and informational presentment related to a selected instrument such as a status tab 910 as shown in an exemplary user interface of FIG. 10B and a notifications tab 912 as shown in an exemplary user interface of FIG. 10C. Information may be displayed in the user interface window such as a graphical representation of the item, a current status, an update timestamp, and current location. In one embodiment, status and a logged history is accessible for a selected item. The logged history may catalog each scan into the system including location of scanning time and date, logged status, user involved, and user comments for each update. Navigational buttons may be available in order to manually change an instrument's status or location. As FIG. 10C shows, a user interface may be configured to permit a user to add or remove notifications and reminders related to the selected instrument. Such things as a status change to "broken" or "missing" can be monitored. Time-based reminders can also be scheduled if an instrument is out for service, in one embodiment.

A change location 914 navigational selection may be made available to a user. Upon selection, a user interface module configured to accept information associated with a location may be presented. In one embodiment a field for user comments may be made available along with an informational module. A shipper (shown as a "Send out for Maintenance" button 916) navigational selection may be made available to a user in one embodiment. Upon selection, a user interface module is presented configured preferably with a list of shipper/carriers from which a user may select. A status change navigational button may be made available to a user in one embodiment. Upon selection, a user may update an item's status including e.g., an "instrument is broken" selection, an "instrument is missing" selection, and a "retire instrument" selection, for example.

Figure 11:
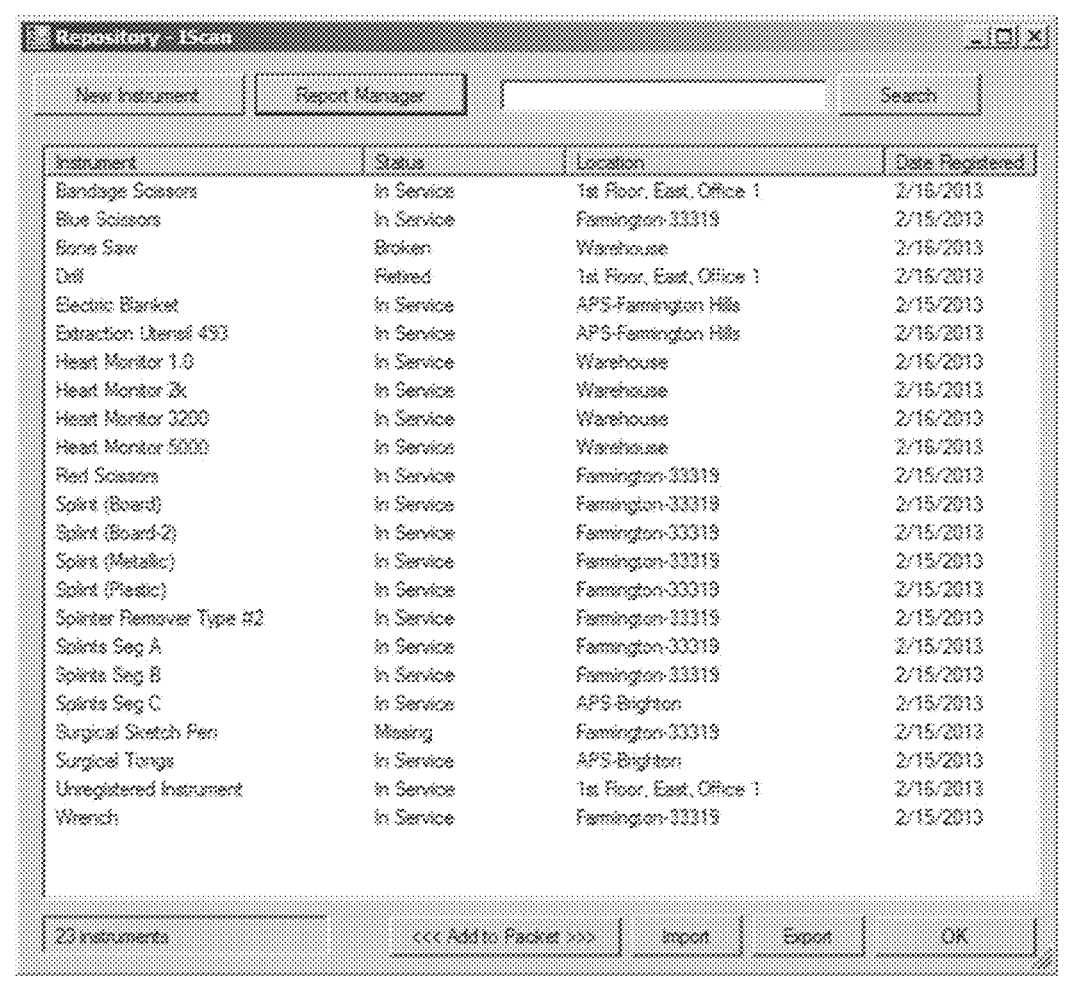

FIG. 11 shows an exemplary information interface for displaying a repository of all items stored in the system 100. Filtering may be made available for quick display of user desired instruments. Filtering may be made available based upon any number of predetermined criteria. Search functions may additionally be made available. In one embodiment, a main panel displays each instrument's name, status, location, and date registered. Items can be edited by user selection, e.g., double-click. Multiple items can also be selected and added to the currently open packet. Other options exist for creating new items, importing/exporting a CSV list of items, or launching the Report Manager.

Figure 12A:
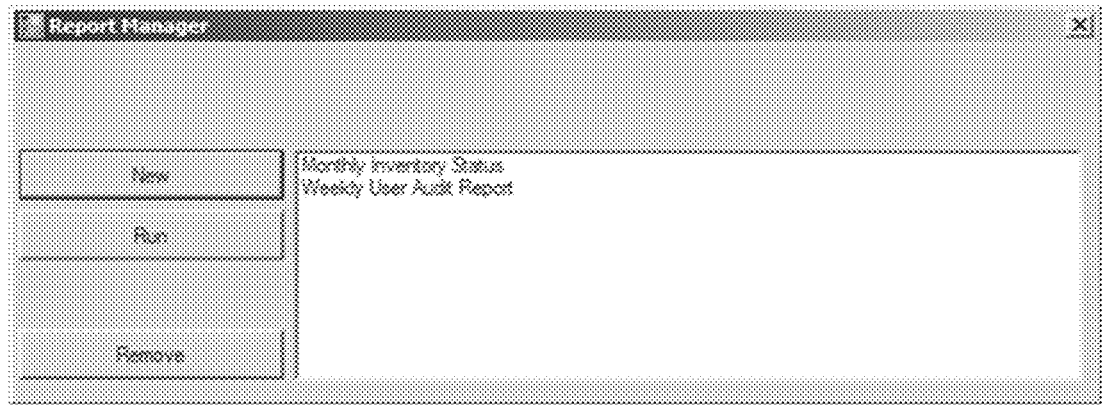
Figure 12B:
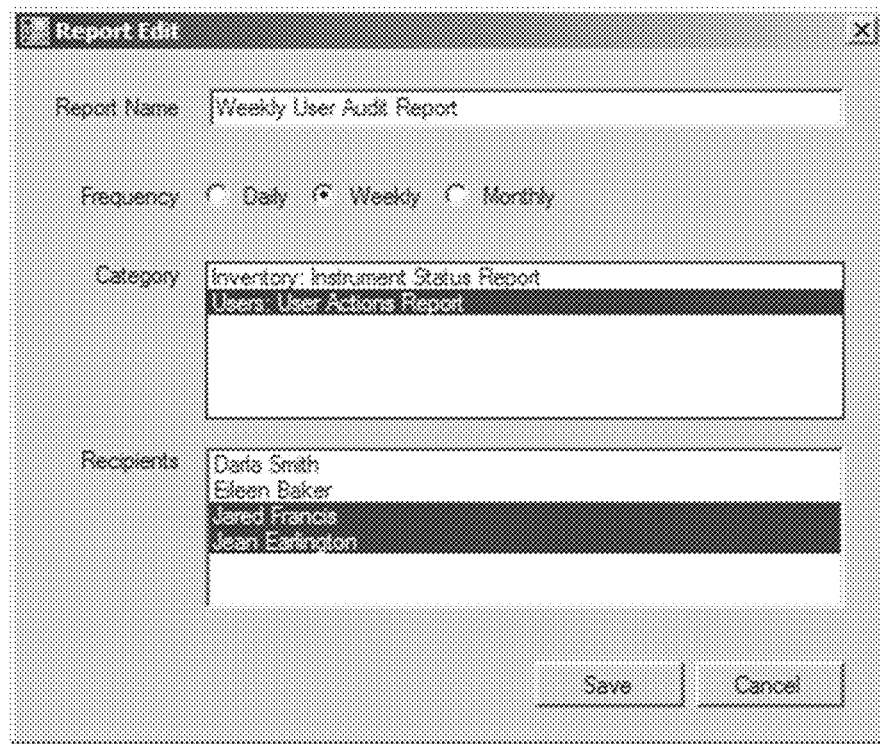

FIGS. 12A and 12B show, exemplary user interfaces for managing reporting functions of the system. FIG. 12A shows a report manager interface configured to generate a scheduled report and amend a list of scheduled reports for generation and delivery. Upon a user selected input, a report can also be selected and run instantly. FIG. 12B shows a user interface for editing a new or existing report. A schedule interval, report type of a predetermined report may be selected, and one or more recipients may be selected for delivery of the associated report.

Figure 13:
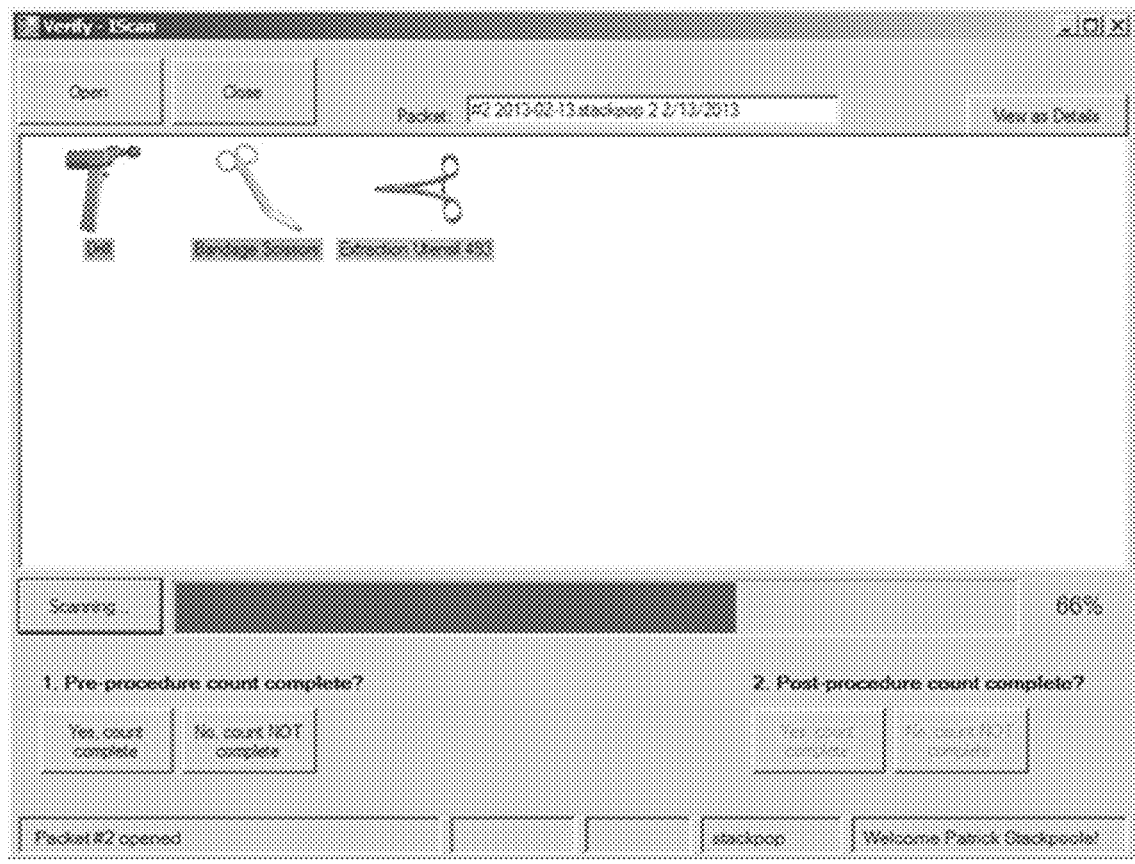

FIG. 13 shows an exemplary user interface for scanning items. The exemplary interface may be accessed to view a particular set of items associated with a surgery set ID consistent with step 815 of FIG. 8 discussed herein above. As FIG. 13 shows, items within a set may be viewed. Scanning for items preferably opens up a progress indicator such as a progress bar. Items found are marked present. In one embodiment, the user may double-click an item to manually mark it as present, missing, broken, or other. When all the items are accounted for, a count can be marked as either complete or not complete. A similar process occurs for the post-procedure count. All user actions are recorded and potentially acted upon by way of notifications and reports.

Figure 14:
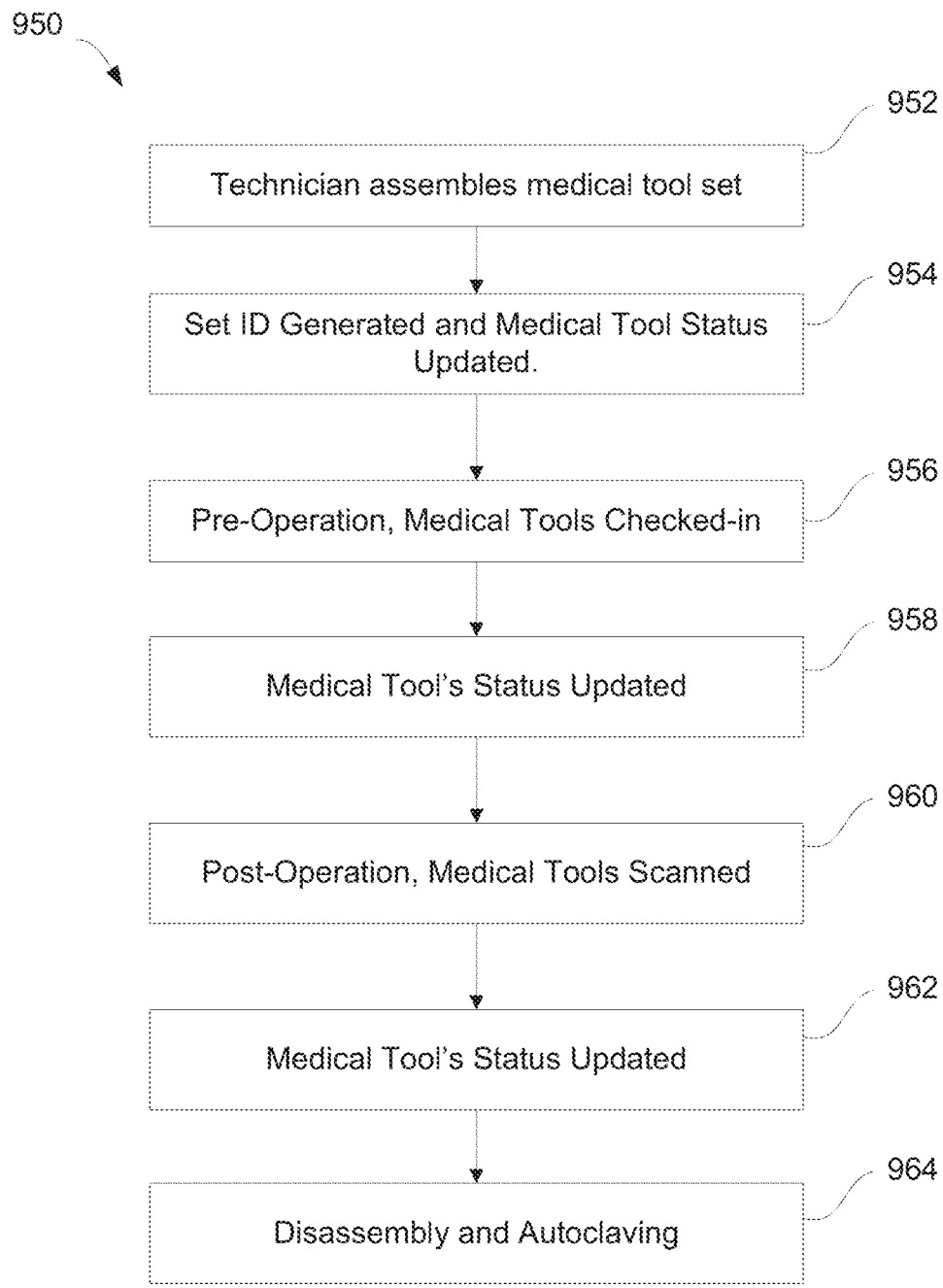
FIG. 14 shows an exemplary process for tracking and managing medical device inventory in an exemplary medical environment, in accordance with the present disclosure.

FIG. 14 shows an exemplary process 950 for tracking and managing medical device inventory in an exemplary medical environment. As FIG. 14 shows, at step 952 the process is initiated by a technician assembling a medical tool set. A unique surgery set ID is generated and, upon scanning in, each medical tool's status is updated in the system. In the exemplary medical environment, the technician may physically move the tools to a pre-operation check-in location. At step 956, the medical tools of the surgery set are again scanned. The medical tool's status is updated in the system 958. In the exemplary medical environment, the operation or procedure is performed. Post-operation, the medical tools are scanned 960 and the medical tool's status updated 962 in the system. Subsequent to scanning and updates in the system, the Technician may then disassemble and perform and necessary autoclaving 964 consistent with procedures of the medical environment.

The disclosure has described certain preferred embodiments and modifications thereto. Further modifications and alterations may occur to others upon reading and understanding the specification. Therefore, it is intended that the disclosure not be limited to the particular embodiment(s) disclosed as the best mode contemplated for carrying out this disclosure, but that the disclosure will include all embodiments falling within the scope of the appended claims.

The invention claimed is:

1. A method of tracking medical devices, tools, and supplies in a medical environment, the method comprising:
registering a plurality of radio frequency identification (RFID) tags with a plurality of medical tools, wherein each medical tool is associated with a RFID tag having a unique identifier and a graphical image representation;
generating an item list comprising a set of medical tools;
wirelessly sensing at least one of the RFID tags associated with an assembled set of medical tools, assembled in preparation of a medical procedure based upon the generated item list;
deciding, if the at least one of the RFID tags associated with the assembled medical tools is sensed, that the medical device or tool is present in the assembled set of the medical tools;
generating a checked-in list of medical tools based upon the deciding;
accounting, in response to a request by a user, medical tools assembled for check-out by wirelessly sensing at least one of the RFID tags associated with the medical tools assembled for check-out;
displaying a list of medical tools associated with the checked-in list and not included in the accounting, wherein each displayed medical tool is graphically represented;
associating the generated item list with a unique identification;
registering a plurality of user-operators;
logging a user-operator upon verification of the user-operator credentials;
associating the wirelessly sensing with a logged user-operator; and
generating a report based upon the unique identification, the report including information based upon the wirelessly sensing and the logged user-operator.

2. The method of claim 1, further comprising:
displaying medical tools of the item list not wirelessly sensed based upon the deciding.

3. The method of claim 1, further comprising:
amending the checked-in list of medical tools during a medical procedure.

4. The method of claim 1, further comprising:
storing a plurality of profiles, wherein each profile is associated with a medical procedure and each profile is associated with a predefined set of medical tools; and
generating the item list based upon a selected profile.

5. The method of claim 1, wherein the wirelessly sensing is executed by a mobile device comprising an RFID reader configured to scan RFID tags.

6. The method of claim 1, wherein the each medical tool is associated with a RFID tag having a unique identifier further comprises adhering the RFID tag having a unique identifier to each medical tool.

7. The method of claim 1, further comprising:
generating a report, in response by a request from a user-operator, the report comprising information of each medical tool associated with a selected unique identification; and
associating each medical tool associated with the selected unique identification with time-stamps corresponding to the wireless sensing and a user-operator performing the wireless sensing.

8. The method of claim 1, further comprising:
selectively generating a report comprising information associated with a quantity of item sets assembled, the item sets associated with a user-operator performing the assembly;
selectively generating a report comprising information associated with a quantity of item sets used; and
selectively generating a report comprising information associated with a quantity of item sets used by a selected user-operator.

9. A computer program product comprising a non-transitory computer readable storage medium storing computer usable program code for performing medical device and tool tracking, the computer program product comprising:

computer usable program code for registering a plurality of radio frequency identification (RFID) tags with a plurality of medical tools, wherein each medical tool is associated with a RFID tag having a unique identifier;

computer usable program code for generating an item list comprising a set of medical tools;

computer usable program code for wirelessly sensing at least one of the RFID tags associated with an assembled set of medical tools, assembled in preparation of a medical procedure based upon the generated item list;

computer usable program code for deciding, if the at least one of the RFID tags associated with the assembled medical tools is sensed, that the medical device or tool is present in the assembled set of the medical tools;

computer usable program code for generating a checked-in list of medical tools based upon the deciding;

computer usable program code for accounting, in response to a request by a user, medical tools assembled for check-out by wirelessly sensing at least one of the RFID tags associated with the medical tools assembled for check-out; and computer usable program code for graphically displaying a list of medical tools associated with the checked-in list and not included in the accounting;

computer usable program code for associating the generated item list with a unique identification;

computer usable program code for registering a plurality of user-operators;

computer usable program code for logging a user-operator upon verification of the user-operator credentials;

computer usable program code for associating the wirelessly sensing with a logged user-operator; and computer usable program code for generating a report based upon the unique identification, the report including information based upon the wirelessly sensing and the logged user-operator.

10. The computer program product of claim 9, further comprising:
computer usable program code for displaying medical tools of the item list not wirelessly sensed based upon the deciding.

11. The computer program product of claim 9, further comprising:
computer usable program code for amending the checked-in list of medical tools during a medical procedure.

12. The computer program product of claim 9, further comprising:
computer usable program code for storing a plurality of profiles, wherein each profile is associated with a medical procedure and each profile is associated with a pre-defined set of medical tools; and
computer usable program code for generating the item list based upon a selected profile.

13. The computer program product of claim 9, wherein the wirelessly sensing is executed by a mobile device comprising an RFID reader configured to scan RFID tags.

14. The computer program product of claim 9, wherein the each medical tool is associated with a RFID tag having a unique identifier further comprises adhering the RFID tag having a unique identifier to each medical tool.

15. The computer program product of claim 9, further comprising:
computer usable program code for generating a report, in response by a request from a user-operator, the report comprising information of each medical tool associated with a selected unique identification; and
computer usable program code for associating each medical tool associated with the selected unique identification with time-stamps corresponding to the wireless sensing and a user-operator performing the wireless sensing.

16. The computer program product of claim 9, further comprising:
computer usable program code for selectively generating a report comprising information associated with a quantity of item sets assembled, the item sets associated with a user-operator performing the assembly;
computer usable program code for selectively generating a report comprising information associated with a quantity of item sets used; and
computer usable program code for selectively generating a report comprising information associated with a quantity of item sets used by a selected user-operator.

17. A medical device tracking system, comprising:
a plurality of radio frequency identification (RFID) tags, wherein each tag is associated with a unique identification identifier, and wherein each tag having a unique identification identifier is coupled to a medical tool;
a computing device configured to display an item list comprising a set of medical tools;
a mobile device comprising a RFID reader, wherein the mobile device is configured to communicate with the computing device and selectively wirelessly sense the RFID tags;
a server computing device communicatively connected to at least the computing device, the server computing device comprising a database configured to store information associated with each medical tool;
wherein the system is configured to:
selectively generate an item list comprising a set of medical tools;
assign a unique identifier to the generated item list;
receive and store scanned RFID tags associated with grouped medical tools, the RFID tags scanned at a first location;
selectively display medical tools remaining to be grouped to complete the generated item list;
generate a checked-in list of medical tools based upon a scan of medical tools at a second location;
generate a checked-out list of medical tools by wirelessly sensing the RFID tags associated with medical tools grouped for check-out; and
display a list of medical tools associated with the checked-in list and not included on the checked-out list;
associating the generated item list with a unique identification;
registering a plurality of user-operators;
logging a user-operator upon verification of the user-operator credentials;
associating the wirelessly sensing with a logged user-operator; and
generating a report based upon the unique identification, the report including information based upon the wirelessly sensing and the logged user-operator.

18. The system of claim 17, further comprising:
a second computing device configured to graphically display the list of medical tools associated with the checked-in list and not included on the checked-out list, wherein the second computing device further comprises a touch screen configured to manipulate display of the list in response to physical input by a user-operator.

* * * * *